United States Patent [19]

Kalamchi

[11] 4,422,451

[45] Dec. 27, 1983

[54] SPINAL COMPRESSION AND DISTRACTION INSTRUMENTATION

[76] Inventor: Ali Kalamchi, 1313 Delaware Ave., Wilmington, Del. 19806

[21] Appl. No.: 360,470

[22] Filed: Mar. 22, 1982

[51] Int. Cl.³ .......................... A61F 5/00; A61B 17/00
[52] U.S. Cl. .................................. 128/69; 128/92 R; 128/92 E; 128/303 R
[58] Field of Search .................. 128/69, 75, 78, 92 R, 128/92 B, 92 E, 92 EA, 303 R, 321

[56] References Cited

U.S. PATENT DOCUMENTS

| | | | |
|---|---|---|---|
| 2,887,111 | 5/1959 | Diaz | 128/321 |
| 4,269,178 | 5/1981 | Keene | 128/69 |
| 4,271,836 | 6/1981 | Bacal et al. | 128/69 X |
| 4,347,845 | 9/1982 | Mayfield | 128/303 R |

FOREIGN PATENT DOCUMENTS

| | | | |
|---|---|---|---|
| 2649042 | 10/1976 | Fed. Rep. of Germany | 128/92 B |
| 825049 | 5/1981 | U.S.S.R. | 128/92 E |

OTHER PUBLICATIONS

"Scoliosis & Spinal Instrumentation Systems", by Zimmer, USA, Inc., 1980-B-2255-4, 10M281, pp. 38-41.
"Wisconsin Compression System", by Zimmer.
"Segmental Spinal Instrumentation", by Edwardo R. Luque, Mexico City, Mexico–Surgical Technique.
"The Rochester Compression System," by DePuy, 1981-38110M, 0601-91.

Primary Examiner—Ronald L. Frinks
Attorney, Agent, or Firm—Connolly and Hutz

[57] ABSTRACT

A hook for spinal compression and distraction instrumentation comprises a main body section having a pair of opposite side surfaces, opposite top and bottom surfaces and opposite front and rear surfaces. A hook portion is connected to and extends from the front surface of the main body section. A longitudinal passageway completely extends through the main body section from the top surface thereof to the bottom surface thereof, and the longitudinal passageway includes front and rear portions. A slotted opening in one of the side surfaces communicates with the front portion of the longitudinal passageway and is positioned closer to the hook portion than the rear portion of the longitudinal passageway. The hook cooperates with a support rod positioned within the longitudinal passageway via the slotted opening in the side surface.

15 Claims, 12 Drawing Figures

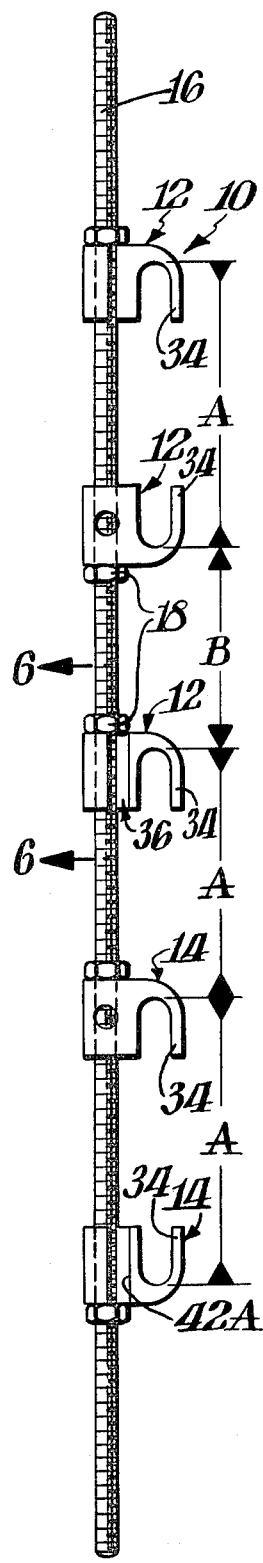
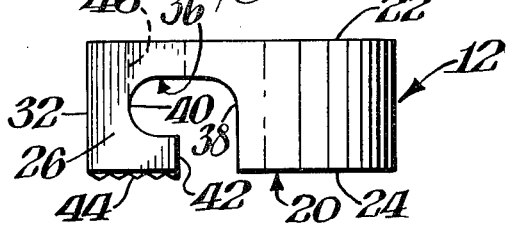
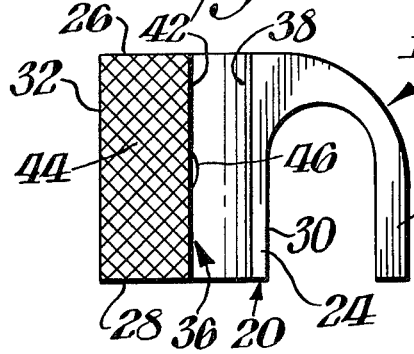
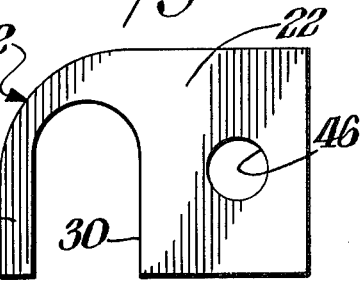
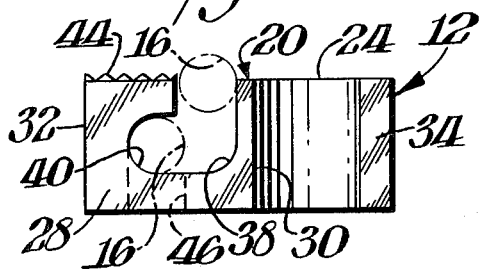
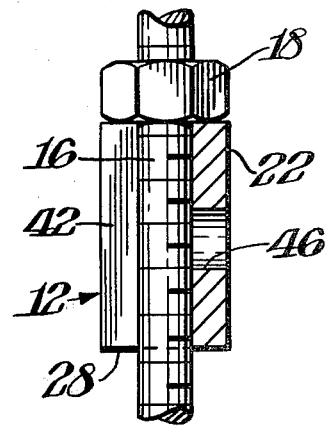
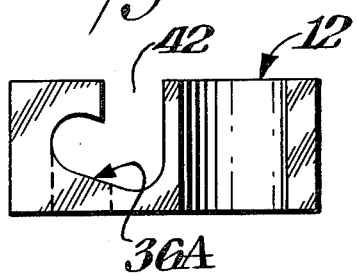
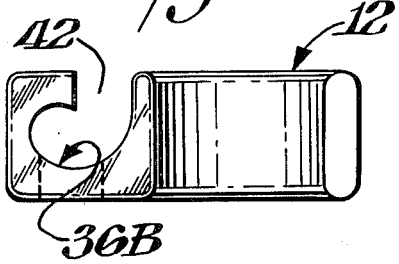

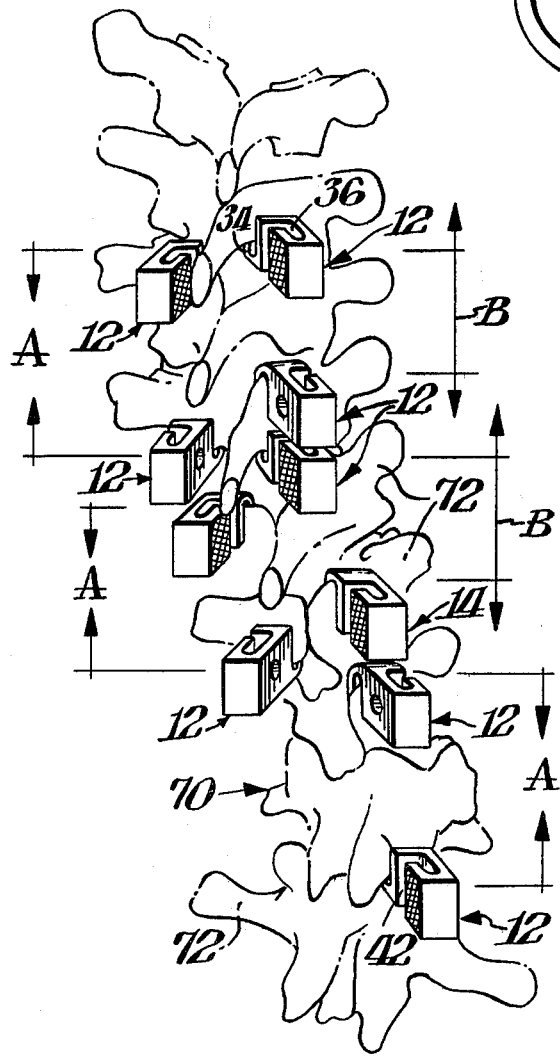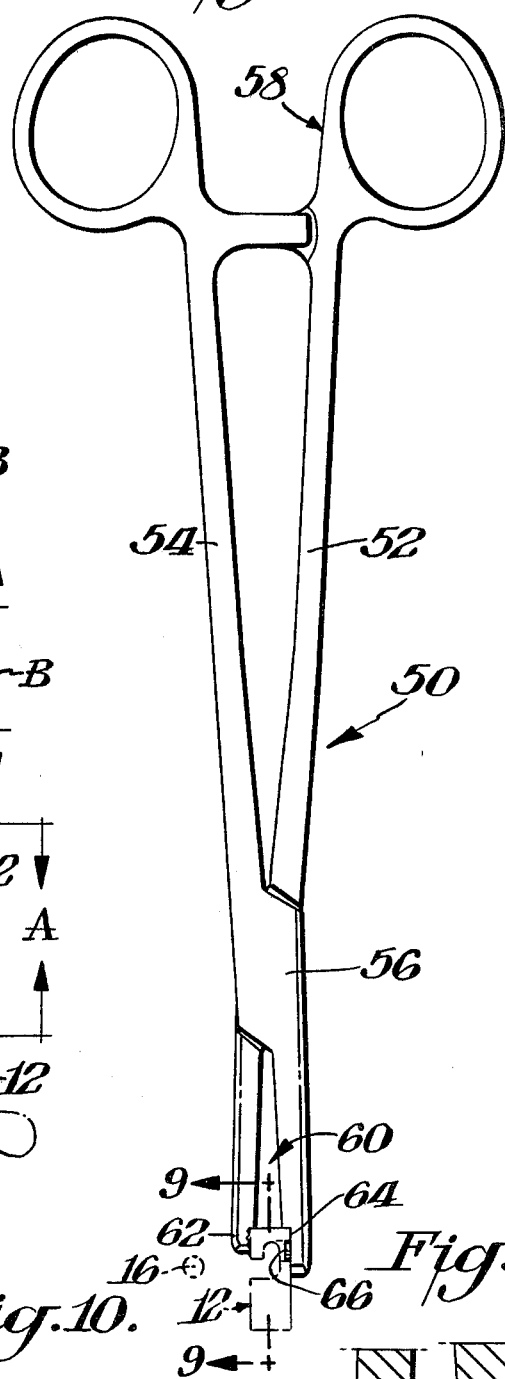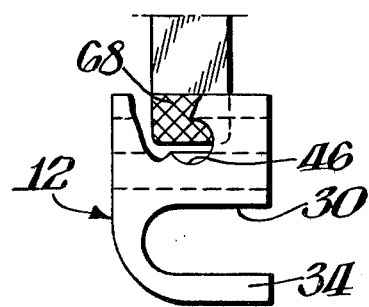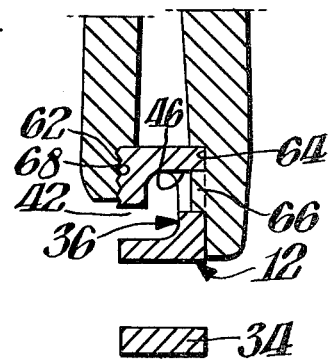

SPINAL COMPRESSION AND DISTRACTION INSTRUMENTATION

BACKGROUND OF THE INVENTION

The present invention relates to instrumentation for spinal deformities and more particularly to spinal hooks, a support rod and locking structure for compressing and/or distracting the spine.

Scoliosis is a lateral deviation of the spinal column. When the spinal curvature exceeds a given limit it becomes necessary to consider surgical treatment. Such surgical treatment is known as arthrodesis and consists of fusing together the vertebrae of the scoliotic curvature after correcting that curvature to the maximum possible extent. Correction can be accomplished prior to surgical treatment by continuous traction of the spine or by corrective plaster casts.

During surgery the correction is completed and finalized. For this purpose, a threaded support rod and hooks are placed on the spinal column for the purpose of straightening the spine and maintaining the correction until arthrodesis is accomplished by means of autogenous bone graft. The heretofore known implants used to correct curvature during surgery include the Harrington system and the system disclosed in U.S. Pat. No. 4,269,178 to Keene, granted May 26, 1981.

Each of the Harrington compression and distraction systems comprises a threaded metal rod and a plurality of hooks having longitudinal passageways therein through which the rod extends. The hooks slide freely along the metal rod and each is adjusted by an internally threaded nut that mates with the rod. Appropriate placement of the hooks on the rod and tightening of the nut affects either compression of the convexity of scoliotic curvature or distraction of the concavity of such curvature. In the Harrington system, the individual hooks are positioned on the threaded rod by inserting either the top or bottom end of the rod into the longitudinal passageway extending through each of the hooks.

The system disclosed in Keene's U.S. Pat. No. 4,269,178 is different from the Harrington system in that it allows special hooks to be tilted and manipulated into position between the vertebrae before the threaded rod engages the hooks. Each of the hooks includes a slot in the rear surface thereof that communicates with the longitudinal passageway within which the threaded rod rests. While this arrangement allows easy placement of the hooks on the rod without threading them onto the rod from the rod ends, a sleeve interlock is required that prevents the threaded rod from being withdrawn out through the slotted opening in the rear surface of the hook. German Auslegeschrift No. 2,649,042 discloses a similar interlock wherein bone screws are prevented from post-operative displacement from either rear or side slotted openings in the screw heads.

SUMMARY OF THE INVENTION

Accordingly, an object of the present invention is a spinal hook for positioning between the spinal vertebrae before engaging its associated support rod and without need for separate interlocking structure to prevent the hook and rod from separating.

Another object of the present invention is a hook holder which permits independent control and manipulation of each spinal hook.

In accordance with the present invention, a hook for spinal compression and distraction instrumentation comprises a main body section having a pair of opposite side surfaces, opposite top and bottom surfaces, and opposite front and rear surfaces. Hook structure is connected to and extends from the front surface of the main body section. A longitudinal passageway completely extends through the main body section from the top surface thereof to the bottom surface thereof, the passageway including front and rear portions. A slotted opening in one of the side surfaces extends from the top surface of the main body section to the bottom surface thereof. The slotted opening communicates with the front portion of the longitudinal passageway and is positioned closer to the hook structure than the rear portion of the passageway.

The hook structure may open in an upward or downward direction. A portion of at least one of the side surfaces of the main body section may be roughened to facilitate handling.

The spinal hook herein is used in combination with a support rod adapted to be positioned within the longitudinal passageway at the rear portion thereof. The support rod has a width slightly less than the width of the slotted opening, and locking structure is arranged to engage the rod and bear upon either the top or the bottom surface of the main body section. Preferably, the rod is externally threaded and the locking structure is an internally threaded nut in meshing engagement with the rod.

A hook holder permits independent control of each hook during placement between the spinal vertebrae and also while the threaded support rod is advanced into the slotted opening in either side of the hook. The hook holder comprises a pair of arms pivoted to one another at a point between the end portions thereof. One end portion of the arms forms a handle and the other end portion forms hook clamping structure including opposite undercut surfaces facing one another. The outer end of one of the arms forming the hook clamping structure is slightly longer than the outer end of the other arm and it has a longer undercut surface thereon. This arrangement enables the hook to be held without blocking the slotted opening. Preferably, at least a portion of one of the undercut surfaces of the hook clamping structure is roughened to facilitate holding a hook.

BRIEF DESCRIPTION OF THE DRAWING

Novel features and advantages of the present invention in addition to those noted above will become apparent to those skilled in the art from a reading of the following detailed description in conjunction with the accompanying drawing wherein:

FIG. 1 is a right side elevational view of spinal compression and distraction instrumentation, according to the present invention;

FIG. 2 is a right side elevational view of a spinal hook, according to the present invention;

FIG. 3 is a left side elevational view of the spinal hook shown in FIG. 2;

FIG. 4 is a top plan view of the spinal hook shown in FIG. 2;

FIG. 5 is a bottom plan view of the spinal hook shown in FIG. 2;

FIG. 6 is a cross-sectional view taken along line 6—6 of FIG. 1;

FIG. 7 is a bottom plan view of an alternate embodiment of spinal hook, according to the present invention;

FIG. 8 is a bottom plan view of a further embodiment of spinal hook, according to the present invention;

FIG. 9 is a side elevational view of a hook holder with a spinal hook clamped therein shown in phantom outline;

FIG. 10 is a cross-sectional view taken along line 9—9 of FIG. 9 with the spinal hook shown in elevation;

FIG. 11 is a fragmental cross-sectional view through the hook clamping end of the holder shown in FIG. 9; and FIG. 12 is a pictorial diagrammatic view illustrating the spinal hooks positioned between the vertebrae for compression and distraction of the spine.

DETAILED DESCRIPTION OF THE INVENTION

Referring in more particularity to the drawing, FIG. 1 illustrates spinal compression and distraction instrumentation 10 for use in correcting spinal deformities, as explained more fully below. The instrumentation 10 comprises a plurality of spinal hooks 12,14, a threaded flexible support rod 16, and locking nuts 18, one nut being associated with each spinal hook. The spinal hooks, support rod, and locking nuts may be formed from stainless steel or other suitable material.

FIGS. 2-5 illustrate a spinal hook 12 comprising a main body section 20 having a pair of opposite side surfaces 22,24. The main body section 20 of the spinal hook has opposite top and bottom surfaces 26 and 28, respectively, and opposite front and rear surfaces 30, 32, respectively. A hook portion 34 is connected to and extends from the front surface 30. As shown best in FIGS. 4 and 5, a longitudinal passageway 36 completely extends through the main body section from the top surface 26 thereof to the bottom surface 28. The longitudinal passageway includes front and rear portions 38 and 40, respectively, and a slotted opening 42 in the side surface 24 communicates with the front portion 38 of the passageway. The slotted opening 42 is positioned in the side wall 24 so that it is closer to the hook portion 34 than the rear portion 40 of the passageway 36.

The spinal hook 14 shown in FIG. 1 is identical to the hook 12 in all respects except that the slotted opening is located in the opposite side wall surface 22. Accordingly, similar reference numerals are used in connection with spinal hook 14, it being understood that the slotted opening 42A is located in side wall 22 whereas the slotted opening 42 of hook 12 is located in the opposite side wall 24.

As is readily apparent from FIG. 1 and the pictorial view of FIG. 12, spinal hooks 12,14 may be positioned on the threaded support rod 16 with the hook portion 34 thereof upwardly or downwardly open. For example, when the hook portion 34 of spinal hook 12 is downwardly open, the slotted opening 42 is positioned on the right side of the instrumentation 10 shown in FIG. 1 as defined by the orientation of FIG. 12. On the other hand, when the hook portion 34 of spinal hook 14 is downwardly open, the slotted opening 42A is on the left side of the instrumentation. Conversely, when the hook portion 34 of the spinal hooks 12,14 is upwardly open, the slotted opening 42 of hook 12 is located on the left side of the instrumentation while opening 42A of hook 14 is positioned on the right side thereof.

The longitudinal passageway 36 which extends through each spinal hook has a substantially uniform cross-section along its length. In the embodiment of the invention shown in FIG. 5, the passageway 36 is elongate and the major axis thereof is along a line that runs from the front surface 30 to the rear surface 32 of the main body section 20. FIG. 7 illustrates a slightly modified embodiment having a different longitudinal passageway 36A. Otherwise the spinal hook shown in FIG. 7 is identical to the structure of FIGS. 2-5. While the cross-section of the longitudinal passageway 36A is elongate, the major axis of that elongate cross-section is angled with respect to the line that runs from the front surface 30 of the rear surface 32 of the main body section 20. This angled configuration functions to guide the support rod 6 to the rear portion 40 of the passageway 36 after the rod engages the passageway from the slotted opening 42.

FIG. 8 illustrates a further embodiment having a longitudinal passageway 36B different from the passageways 36 and 36A. Otherwise, the spinal hook shown in FIG. 7 is substantially identical to the structure of FIGS. 2-5 and FIG. 7. The cross-section of the longitudinal passageway 36B provides a sweeping curve for guiding the support rod 6 into the passageway to the rear portion thereof.

Spinal hooks 12 and 14 may further include a roughened area 44 on at least a portion of one of the opposite side surfaces 22,24 of the main body section 20. Preferably, the roughening may be in the form of crisscrosses or vertical serrations, and such roughening may be located on the side surface adjacent to the slotted opening. With spinal hook 12, the roughening is on the side surface 24 adjacent slotted opening 42, and with spinal hook 14, the roughening is on side surface 22 adjacent slotted opening 42A. Also, in the side surface of the spinal hook opposite the slotted opening, a central hole 46 is provided. As explained more fully below, the roughening 44 and central hole 46 cooperate with complementary structure on a hook holder designed to clamp onto the hook and assist in controlling and manipulating the hook into position on the spine.

A hook holder 50 according to the present invention is illustrated in FIGS. 9-11 of the drawing. The holder includes a pair of arms 52,54 pivoted to one another at a point 56 between the end portions thereof. One end portion of the arms 52,54 forms a handle 58 while the other end portion forms hook clamping structure 60. The hook clamping structure of the holder 50 includes opposite undercut surfaces 62,64 facing one another, as shown best in FIGS. 9 and 11. Also, as shown in these Figures, the undercut surface 64 is longer than the undercut surface 62 and includes a central projection 66 extending therefrom. The spinal hook is positioned between the clamping structure 60 of the holder so that the central projection 66 on the longer undercut surface 64 is positioned within the central hole 46 in the side surface of the spinal hook. Moreover, the shorter undercut surface 62 may be roughened at 68 in such a manner that it mates with the roughening on the side surface of the spinal hook opposite the one in which the hole 46 is located. Also important is the fact that the rear surface 32 of the spinal hook snugly engages the hook holder precisely at the beginning of the undercut surfaces 62,64 which prevents the hook from moving relative to the holder once it is clamped therein.

The spinal compression and distraction instrumentation 10 of the present invention is utilized for surgical treatment of spinal fractures or for straightening of the spine in the surgical treatment for deviations of the spinal column, especially scoliosis. Appropriate placement of the spinal hooks between the vertebrae is used to compress the convexity of scoliotic curvature or distract the concavity of such curvature. Alternatively, both compression and distraction may be accomplished at the same time at different locations along the spine.

Referring first to FIG. 1, the upper two spinal hooks 12 on the threaded support rod 16 face one another with the lower hook portion 34 upwardly open and the higher hook downwardly open. When the locking nuts 18 are positioned as shown and tightened, the upper two spinal hooks move toward one another thereby placing in compression A any material between them. Compression A is also achieved between the lowermost pair of spinal hooks 14 on the support rod 16, and also when the middle spinal hook 12 is urged in a downward direction.

Distraction B is accomplished by urging a spinal hook away from an adjacent spinal hook, and such distraction B is illustrated in FIG. 1 between the third and fourth highest spinal hooks on the support rod. As is clear from the drawing, upon tightening of the locking nuts 18 these spinal hooks move away from one another, thereby placing in distraction B any material betweem them.

The assembled spinal hooks 12,14, support rod 16, and locking nuts 18 are arranged so that the support rod is seated at the rear portion 40 of the longitudinal passageway 36 of each spinal hook. Since the tendency of the rod is to move to the rear portion of the passageway when the locking nuts are tightened, such positioning prevents the hook and rod from separating. Also, to aid in the prevention of such separation, the slotted openings 42,42A of adjacent spinal hooks in the final assembly are located on opposite sides of that assembly. Every other spinal hook in the final assembly has a slotted opening on one side thereof while the other spinal hooks have their slotted openings on the opposite side of the assembly.

Turning now to FIG. 12, spinal hooks 12,14 are shown at appropriate locations along a spinal column 70 comprising individual vertebrae 72. Placement of the spinal hooks is accomplished by initially clamping a hook between the undercut clamping surfaces 62,64 of the hook holder 50. The projection 66 on the hook holder engages the hole 46 in the spinal hook. Additionally when the roughening feature is incorporated, the roughening on undercut surfaces 62 of the holder engages the roughening 44 on the side surface of the spinal hook. The holder is then used to position the spinal hook at the purchase site around the transverse process or vertebrae 72. The hook holder and hook remain at that position on the spine until the other spinal hooks in the column have been similarly positioned, and the support rod manipulated to interconnect the hooks. Alternatively, a sharp spinal hook may be used first to form the purchase sites after which the spinal hooks 12,14 are positioned at those sites with the aid of the hook holders.

Once the spinal hooks are appropriately positioned on the right side of the spinal column as shown in FIG. 12, it being understood that a hook holder is associated with each of them, the threaded support rod 16 and locking nuts 18 are brought into engagement with the hooks. For example, the rod 16 is urged into the left side slotted opening 42 of the lowermost spinal hook 12 and is ultimately positioned at the rear portion 40 of the passageway 36. A locking nut 18 is positioned to bear upon the top surface 22 of the inverted spinal hook 12. Similarly, the support rod is urged into the right side slotted opening 42 of the next spinal hook in the assembly, and a locking nut 18 is arranged on the support rod 16 so that it bears upon the top surface 26 of that upright hook. Appropriate tightening of the locking nuts 18 advances the pair of lowermost spinal hooks toward one another thereby applying compression A to the spinal vertebrae located between these hooks. The support rod engages the other spinal hooks in the assembly in similar fashion, and the locking nuts 18 are tightened to achieve either compression A or distraction B. The hook holders may be removed after the locking nuts are tightened.

Once it is determined where the compression and distraction is to be applied along the spinal column 70, the particular spinal hooks 12,14 are selected so that adjacent spinal hooks have their slotted openings on opposite sides. By positioning the support rod at the rear portion 40 of the longitudinal passageway of each spinal hook and by having alternate side slotted openings, stability is achieved and the threaded support rod is prevented from being inadvertently or otherwise withdrawn from the spinal hooks.

FIG. 12 also illustrates a second assembly of spinal hooks 12 arranged between the vertebrae 72 at the left side of the spinal column in order to achieve compression A at those areas where distraction B is accomplished on the right side of the spine.

What is claimed:

1. A hook for spinal compression and distraction instrumentation comprising a main body section having a pair of opposite side surfaces, opposite top and bottom surfaces, and opposite front and rear surfaces, hook means connected to and extending from the front surface of the main body section, a longitudinal passageway completely extending through the main body section from the top surface thereof to the bottom surface thereof, the longitudinal passageway including front and rear portions, and a slotted opening in one of the side surfaces extending from the top surface of the main body section to the bottom surface thereof, the slotted opening communicating with the front portion of the longitudinal passageway and positioned closer to the hook means than the rear portion of the longitudinal passageway.

2. A hook as in claim 1 wherein the hook means is upwardly open.

3. A hook as in claim 1 wherein the hook means is downwardly open.

4. A hook as in claim 1 wherein the longitudinal passageway has a substantially uniform cross-section throughout its length.

5. A hook as in claim 4 wherein the cross-section of the longitudinal passageway is elongate and the major axis of the elongate cross-section is along a line that runs from the front surface to the rear surface of the main body section.

6. A hook as in claim 4 wherein the cross-section of the longitudinal passageway is elongate and the major axis of the elongate cross-section is angled with respect to a line that runs from the front surface to the rear surface of the main body section.

7. A hook as in claim 1 wherein a portion of at least one of the opposite side surfaces of the main body section is roughened to facilitate handling.

8. A hook as in claim 1 wherein at least one of the opposite side surfaces of the main body section includes a central hole.

9. A hook as in claim 1 in combination with a support rod adapted to be positioned within the longitudinal passageway at the rear portion thereof, the support rod having a width slightly less than the width of the slotted opening, and locking means engaging the rod and arranged to bear upon either the top or bottom surface of the main body section.

10. The combination of claim 9 including a second hook on the support rod, the hooks having slotted openings on opposite sides.

11. The combination of claim 9 wherein the support rod is externally threaded and the locking means is an internally threaded nut in meshing engagement with the rod.

12. A hook holder comprising a pair of arms pivoted to one another at a point between the end portions thereof, one end portion of the arms forming handle means and the other end portion forming hook clamping means including opposite undercut surfaces facing one another, the outer end of one of the arms forming the hook clamping means being slightly longer than the outer end of the other arm and having a longer undercut surface thereon.

13. A hook holder as in claim 12 wherein at least a portion of one of the undercut surfaces of the hook clamping means is roughened to facilitate holding a hook.

14. A hook holder as in claim 12 wherein the longer undercut surface includes a central projection thereon.

15. A hook holder as in claim 14 in combination with a spinal hook having opposite side surfaces, and a central hole in one of the side surfaces constructed and arranged to receive the central projection on the longer undercut surface of the hook holder.

* * * * *